US011717267B2

(12) United States Patent
Hwang et al.

(10) Patent No.: US 11,717,267 B2
(45) Date of Patent: Aug. 8, 2023

(54) HOLLOW CYLINDRICAL ULTRASOUND IMAGING SYSTEM FOR ANALYZING BODY COMPOSITION AND OPERATION METHOD OF THE ULTRASOUND IMAGING SYSTEM

(71) Applicant: DAEGU GYEONGBUK INSTITUTE OF SCIENCE AND TECHNOLOGY, Daegu (KR)

(72) Inventors: Jae Youn Hwang, Daegu (KR); Chun Yeol You, Seoul (KR); Moon Hwan Lee, Gyeongsan-si (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 98 days.

(21) Appl. No.: 17/458,737

(22) Filed: Aug. 27, 2021

(65) Prior Publication Data

US 2022/0071598 A1 Mar. 10, 2022

(30) Foreign Application Priority Data

Sep. 4, 2020 (KR) ........................ 10-2020-0113043

(51) Int. Cl.
*A61B 8/00* (2006.01)
*A61B 8/08* (2006.01)
*A61B 8/12* (2006.01)

(52) U.S. Cl.
CPC ................ *A61B 8/483* (2013.01); *A61B 8/12* (2013.01); *A61B 8/5207* (2013.01); *A61B 8/54* (2013.01); *A61B 2562/0247* (2013.01)

(58) Field of Classification Search
CPC ......... A61B 8/483; A61B 8/12; A61B 8/5207; A61B 8/54; A61B 2562/0247
See application file for complete search history.

(56) References Cited

U.S. PATENT DOCUMENTS 7,521,708 B1 * 4/2009 Agassi ............... G01R 33/0354
257/38
2005/0143638 A1 * 6/2005 Johnson ................. A61B 5/415
600/407

(Continued)

FOREIGN PATENT DOCUMENTS

JP 2020503142 1/2020
KR 10-2016-0061878 6/2016

(Continued)

OTHER PUBLICATIONS

Haeyun Lee et al., "Channel Attention Module With Multiscale Grid Average Pooling for Breast Cancer Segmentation in an Ultrasound Image", IEEE Transactions on Ultrasonics, Ferroelectrics, and Frequency Control, vol. 67, No. 7, Jul. 2020.

*Primary Examiner* — Serkan Akar
*Assistant Examiner* — Amal Aly Farag
(74) *Attorney, Agent, or Firm* — Lex IP Meister, PLLC

(57) ABSTRACT

Disclosed are an ultrasound imaging system for analysis of a body composition and an operation method of an ultrasound imaging system which is designed for analysis of a body composition. An ultrasound imaging system may include: a scan device into which an object is insertable; an ultrasonic probe connected to a part of the scan device; a controller configured to control the ultrasonic probe to emit a transmission ultrasonic signal to the object at multiple positions at the scan device, and receive a reflection ultrasonic signal reflected from the object; and an image processor configured to generate multiple 2D ultrasound images based on reflection ultrasonic signals received at the multiple positions at the scan device, respectively, and generate a 3D ultrasound image based on the multiple 2D ultrasound images.

12 Claims, 13 Drawing Sheets

(56) References Cited

U.S. PATENT DOCUMENTS

| | | | |
|---|---|---|---|
| 2012/0029358 A1* | 2/2012 | Lin | A61B 8/0825 600/447 |
| 2015/0051490 A1* | 2/2015 | McKinnon | A61B 8/14 600/443 |
| 2019/0015059 A1* | 1/2019 | Itu | G06T 7/143 |
| 2019/0049540 A1* | 2/2019 | Odry | G06N 3/084 |
| 2020/0046322 A1* | 2/2020 | Silberman | A61B 8/465 |

FOREIGN PATENT DOCUMENTS

| | | |
|---|---|---|
| KR | 10-2017-0108461 | 9/2017 |
| KR | 10-2018-0096493 | 8/2018 |
| KR | 10-2020-0073965 | 6/2020 |

* cited by examiner

[FIG. 1]
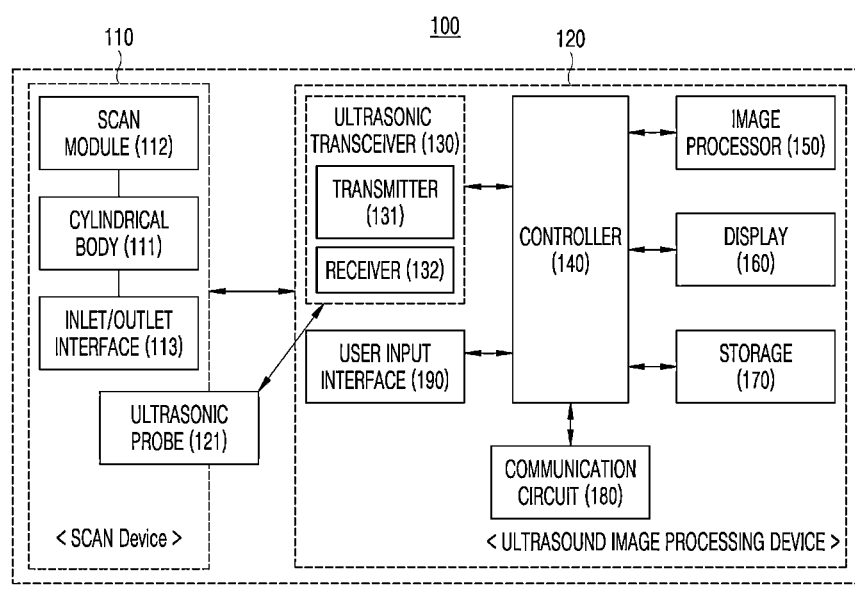

[FIG. 2]
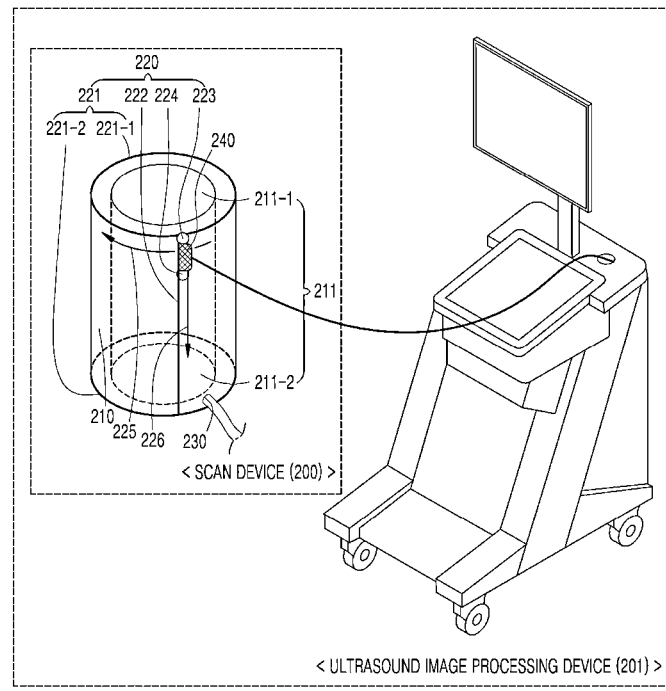
[FIG. 3]
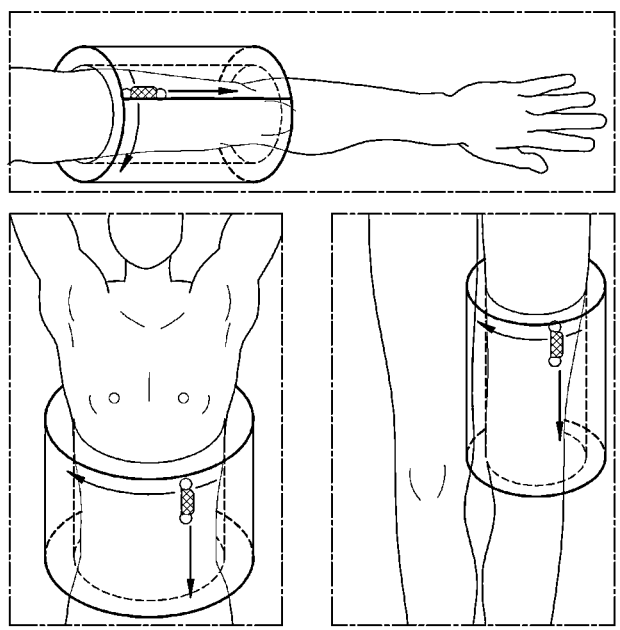

[FIG. 4]
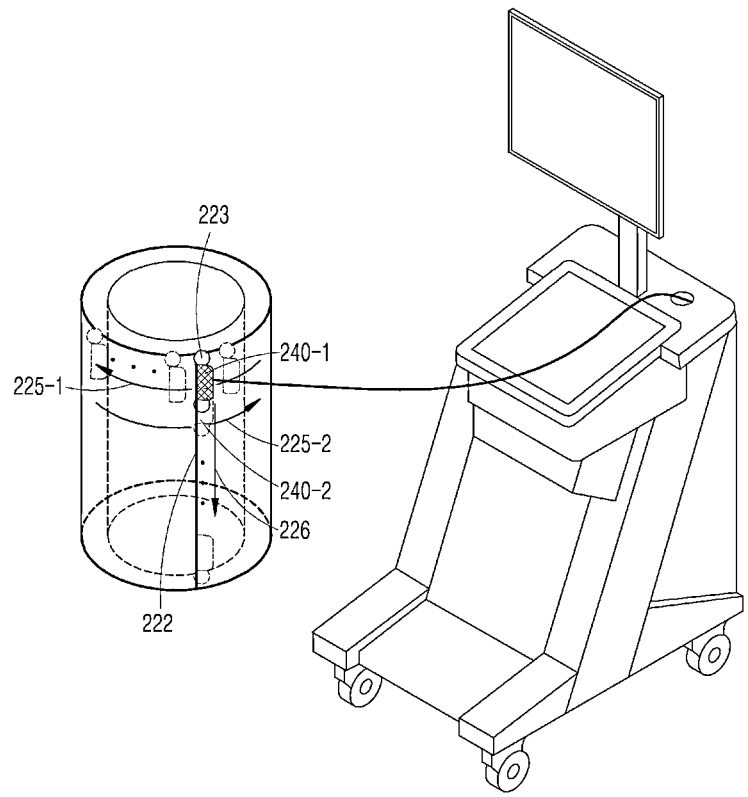
[FIG. 5]
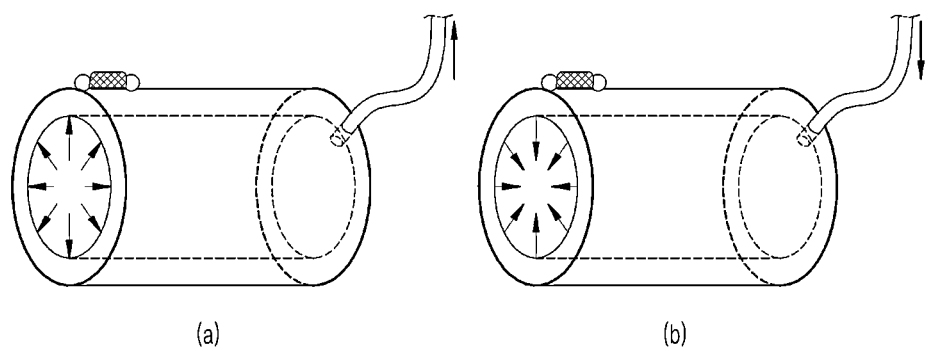
(a)              (b)

[FIG. 6]
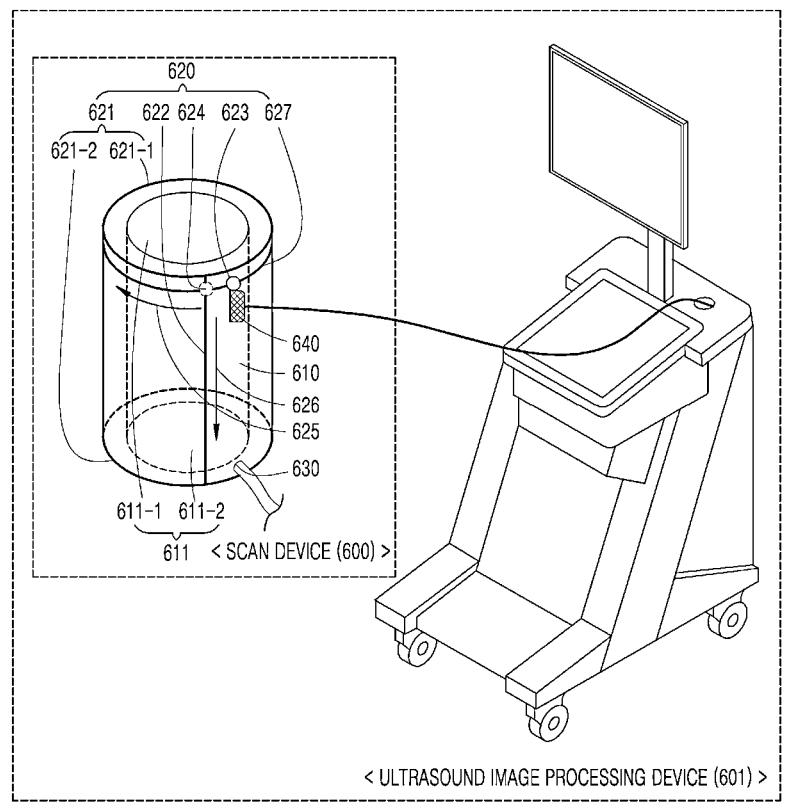

[FIG. 7]
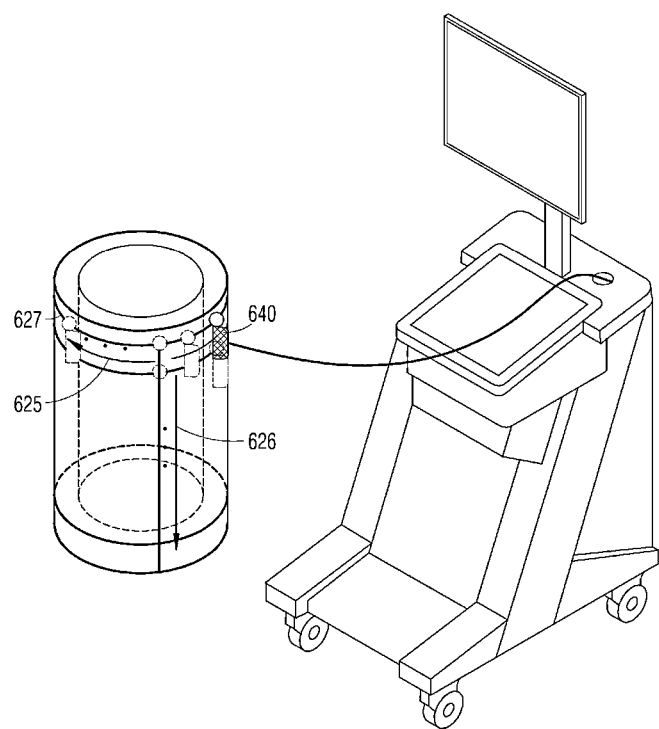

[FIG. 8]
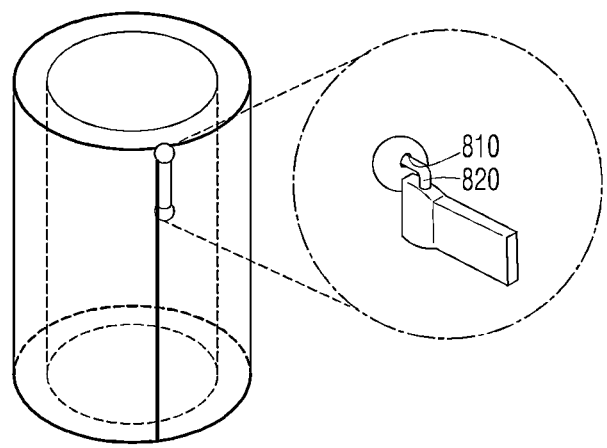
[FIG. 9]
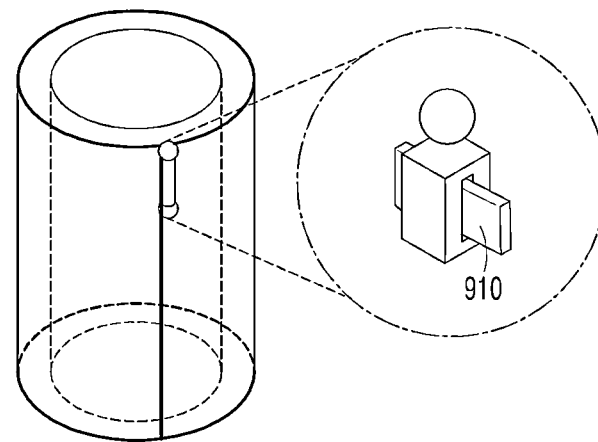

[FIG. 10A]
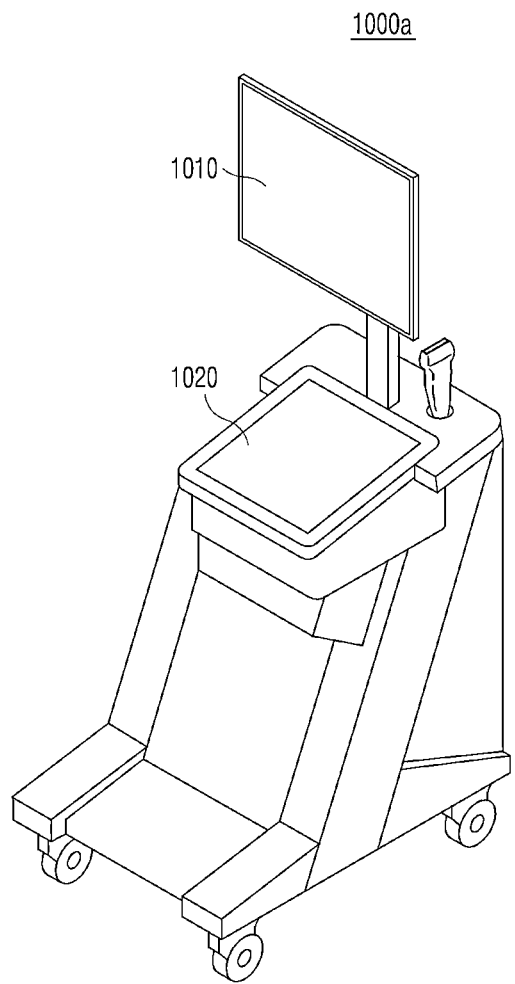

[FIG. 10B]
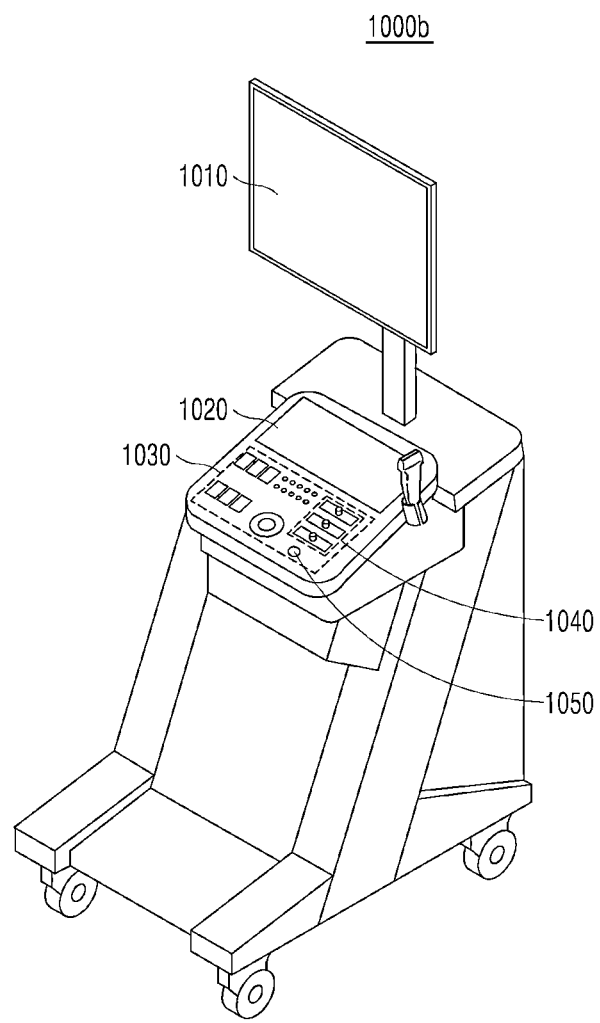

[FIG. 11]
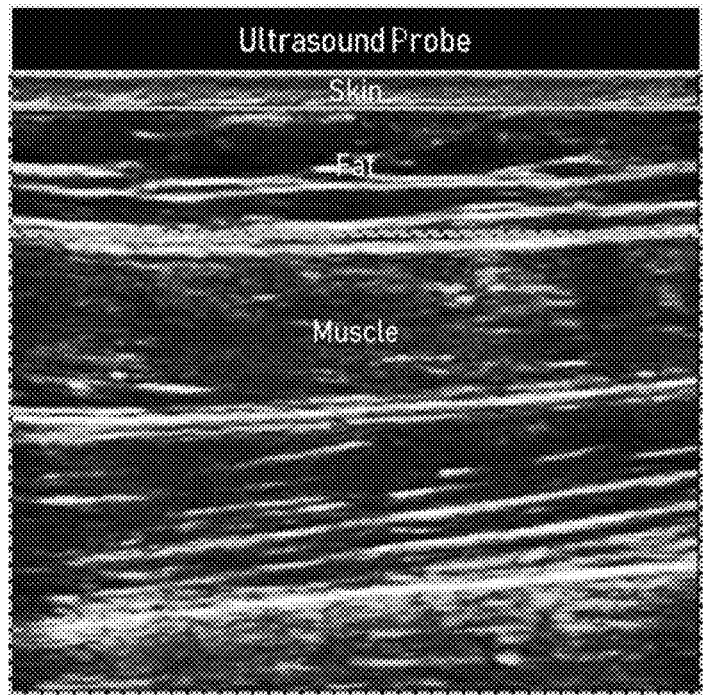
[FIG. 12]
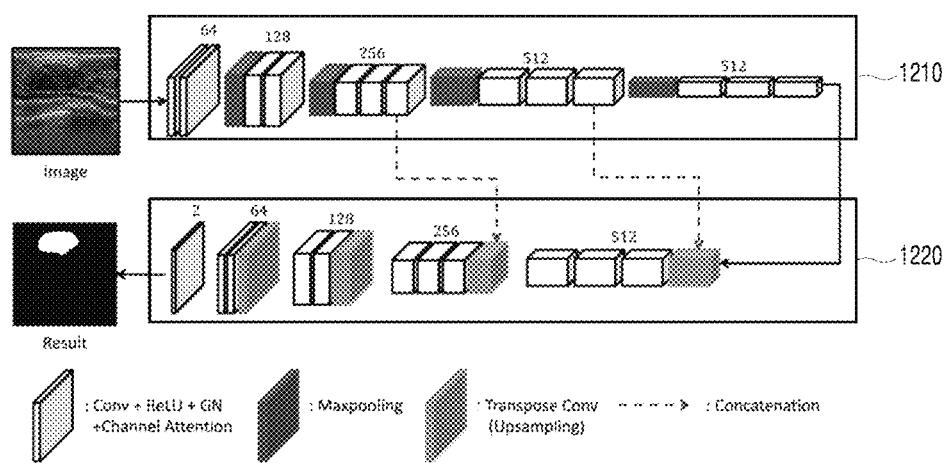

[FIG. 13]
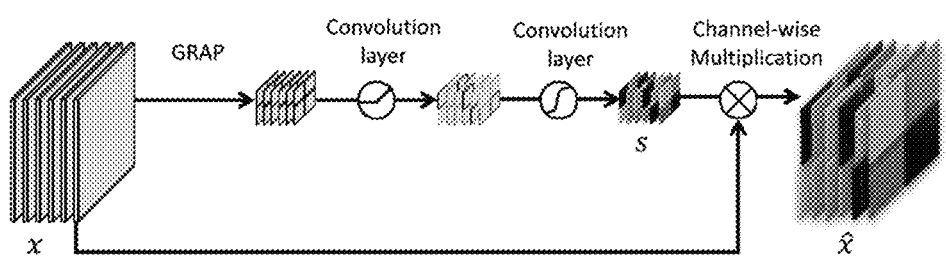
Channel attention module with GRAP.
[FIG. 14]
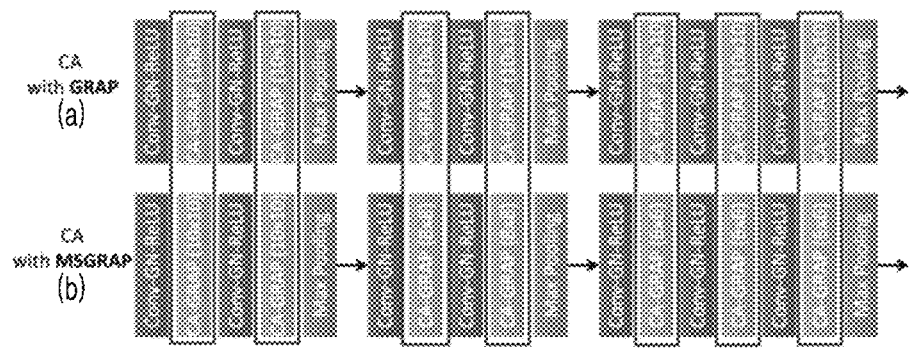

[FIG. 15]

| AUMethods | Global Acc. | F1 score | Sensitivity(Recall) | Specificity | FPR | Precision | IoU | AUC(PR) | AUC(ROC) |
|---|---|---|---|---|---|---|---|---|---|
| FCN [16] | 97.384 | 0.7123 | 0.7702 | 0.9834 | 0.0166 | 0.6907 | 0.5627 | 0.7812 | 0.9634 |
| U-Net [18] | 97.435 | 0.7132 | 0.7846 | 0.9827 | 0.0173 | 0.6696 | 0.5613 | 0.7579 | 0.9532 |
| SegNet [17] | 97.576 | 0.7225 | 0.8006 | 0.9802 | 0.0198 | 0.6877 | 0.6001 | 0.7952 | 0.9604 |
| PSPNet-18 [20] | 97.736 | 0.7520 | 0.8088 | 0.9847 | 0.0153 | 0.7058 | 0.6058 | 0.8047 | 0.9510 |
| ENCNet-18 [35] | 97.597 | 0.7266 | 0.7990 | 0.9834 | 0.0166 | 0.6859 | 0.5770 | 0.7511 | 0.9647 |
| Ours-GAP | 97.462 | 0.7205 | 0.7638 | 0.9840 | 0.0160 | 0.6983 | 0.5993 | 0.7818 | 0.9490 |
| Ours-GRAP | 97.632 | 0.7445 | 0.7769 | 0.9852 | 0.0148 | 0.7276 | 0.6185 | 0.8084 | 0.9551 |
| Ours-MSGRAP | 97.794 | 0.7658 | 0.8041 | 0.9866 | 0.0134 | 0.7459 | 0.6226 | 0.8149 | 0.9606 |

[FIG. 16]
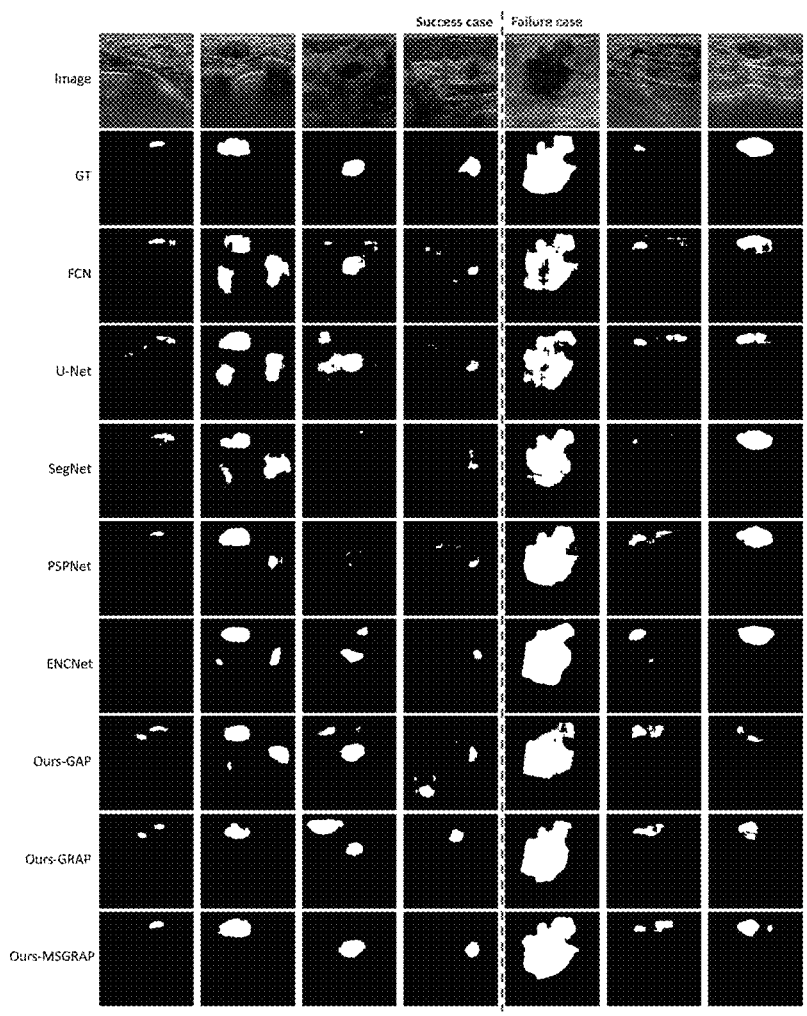

[FIG. 17]
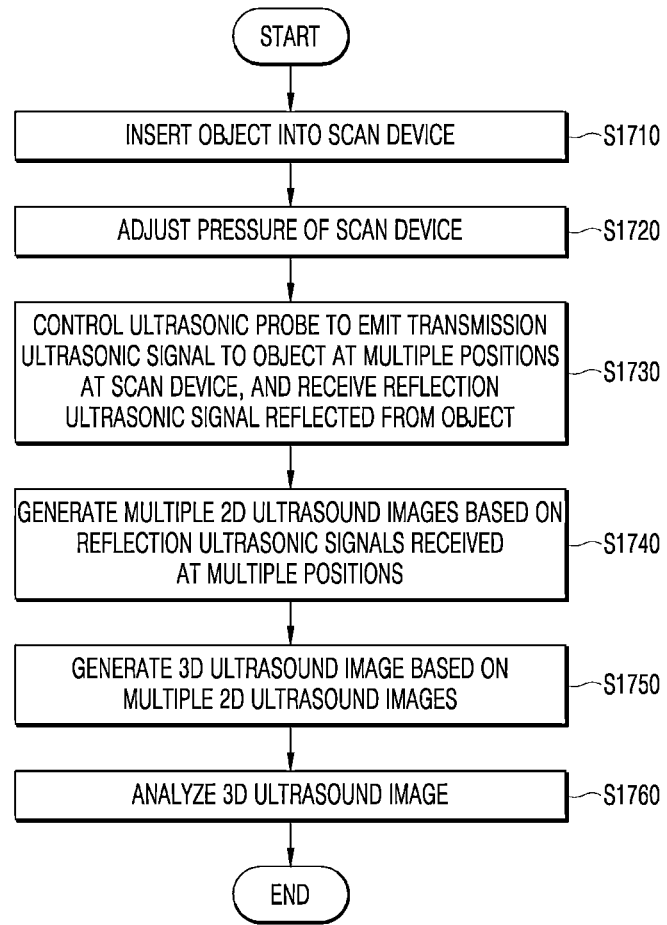

HOLLOW CYLINDRICAL ULTRASOUND IMAGING SYSTEM FOR ANALYZING BODY COMPOSITION AND OPERATION METHOD OF THE ULTRASOUND IMAGING SYSTEM

CROSS-REFERENCE TO RELATED APPLICATIONS

This present application claims benefit of priority to Korean Patent Application No. 10-2020-0113043, entitled "ULTRASOUND IMAGING SYSTEM AND METHOD FOR OPERATING OF ULTRASOUND IMAGING SYSTEM FOR ANALYZING BODY COMPOSITION," filed on Sep. 4, 2020, in the Korean Intellectual Property Office, the entire disclosure of which is incorporated herein by reference.

STATEMENT REGARDING GOVERNMENT SUPPORT

This invention was supported at least in part by Ministry of Trade, Industry and Energy of South Korean government for research project, the title of which is "Smart Monitoring System Development for implant liner of Orthopedic artificial hip joint" (Project Number: 1415163851) managed by KEIT (Korea Evaluation Institute of Industrial Technology).

Also, this invention was supported at least in part by Ministry of Trade, Industry and Energy of South Korean government for research project, the title of which is "Development of age-friendly wearable smart healthcare system and service for real-time quantitative monitoring of urination and defecation disorders" (Project Number: 1415173934) managed by KEIT (Korea Evaluation Institute of Industrial Technology).

BACKGROUND OF THE INVENTION

1. Field of the Invention

The present disclosure relates to a technology for easily generating a three-dimensional (3D) ultrasound image of an object by using a scan device which can transmit an ultrasonic signal to the object at multiple positions at the object and receive a signal reflected from the object.

2. Description of the Prior Art

An ultrasound image processing device can transmit an ultrasonic signal to an object (e.g., a human body) through an ultrasonic probe, receive an ultrasonic signal reflected from the object, and then generate an ultrasound image of the object by using the received ultrasonic signal.

Such an ultrasound image processing device can generate a two-dimensional (2D) ultrasound image, as an ultrasound image of an object, and if the device is an ultrasonic diagnostic device, the device can diagnose a lesion based on a generated ultrasound image of a human body.

However, the ultrasound image processing device has a limitation in identifying a three-dimensional shape of an object with a big size.

A prior art (Korean Patent Application Publication No. 10-2020-0073965) discloses a feature of acquiring multiple frequency band images having different frequency bands from ultrasonic signals corresponding to an object and based on the brightness of each area including the object, synthesizing the multiple frequency band images, thereby generating a clear ultrasound image. However, the above prior art does not disclose a feature of generating a 3D ultrasound image of an object and analyzing the generated 3D ultrasound image.

Therefore, a technology capable of easily generating a 3D ultrasound image of a large object is required.

SUMMARY OF THE INVENTION

An embodiment of the present disclosure is directed to, by using a scan device capable of transmitting or receiving an ultrasonic signal to or from an object at multiple positions, generating multiple 2D ultrasound images of the object, and easily generating a 3D ultrasound image of the object based on the multiple 2D ultrasound images.

An embodiment of the present disclosure is directed to generating a 3D ultrasound image by using a 1D array-type probe as an ultrasonic probe connected to a scan device, and thus to reducing costs by using a lower-cost ultrasonic probe.

An embodiment of the present disclosure is directed to, by using, in a scan device, a cylindrical body made of a flexible material and an ultrasonic wave-transmitting material, adjusting the amount of a fluid in the cylindrical body to enable smooth transmission or reception of an ultrasonic signal between an object and an ultrasonic probe through the cylindrical body in a state in which the scan device is in close contact with the object, regardless of the type of object (e.g., an arm, a leg, or an abdomen part of a human body) inserted in the scan device, the volume of the object, or a state of a surface (e.g., an uneven surface).

An embodiment of the present disclosure is directed to enabling use of a conventional ultrasonic probe in generating a 3D ultrasound image, by configuring a scan device to or from which an ultrasonic probe can be attached or detached.

An embodiment of the present disclosure is directed to analyzing body compositions of an object, a three-dimensional distribution of the body compositions, or a three-dimensional shape of fat and muscle based on a 3D ultrasound image of the object.

In addition, an embodiment of the present disclosure is directed to precisely recognizing an internal shape of an object, such as a muscle layer, a fat layer, etc., in a 3D ultrasound image, based on a deep learning model for semantic segmentation of target regions.

The present disclosure may provide an ultrasound imaging system and an operation method of the ultrasound imaging system, wherein a three-dimensional (3D) ultrasound image of an object is easily generated by using a scan device capable of transmitting an ultrasonic signal to the object at multiple positions, and receiving a signal reflected from the object.

An embodiment of the present disclosure may provide an ultrasound imaging system including: a scan device into which an object is insertable; an ultrasonic probe connected to a part of the scan device; a controller configured to control the ultrasonic probe to emit a transmission ultrasonic signal to the object at multiple positions at the scan device, and receive a reflection ultrasonic signal reflected from the object; and an image processor configured to generate multiple two-dimensional (2D) ultrasound images based on reflection ultrasonic signals received at the multiple positions at the scan device, respectively, and generate a 3D ultrasound image based on the multiple 2D ultrasound images.

In addition, an embodiment of the present disclosure may provide an operation method of an ultrasound imaging system, the method including: inserting an object into a scan device; controlling the ultrasonic probe connected to a part of the scan device to emit a transmission ultrasonic signal to the object at multiple positions at the scan device, and receive a reflection ultrasonic signal reflected from the object; and generating multiple 2D ultrasound images based on reflection ultrasonic signals received at the multiple positions at the scan device, respectively, and generating a 3D ultrasound image based on the multiple 2D ultrasound images.

Aspects, features, and advantages other than those described above will become apparent from the following drawings, claims, and detailed description of the present disclosure.

According to embodiments of the present disclosure, by using a scan device capable of transmitting or receiving an ultrasonic signal to or from an object at multiple positions, multiple 2D ultrasound images of the object can be generated, and a 3D ultrasound image of the object can be easily generated based on the multiple 2D ultrasound images.

According to embodiments of the present disclosure, by using a 1D array-type probe as an ultrasonic probe connected to a scan device, a 3D ultrasound image can be generated, and thus money can be saved by using a lower-cost ultrasonic probe.

According to embodiments of the present disclosure, by using, in a scan device, a cylindrical body made of a flexible material and an ultrasonic wave-transmitting material, the amount of a fluid in the cylindrical body can be adjusted so as to enable smooth transmission or reception of an ultrasonic signal between an object and an ultrasonic probe through the cylindrical body in a state where the scan device is in close contact with the object, regardless of the type of object (e.g., an arm, a leg, or an abdomen part of a human body) inserted in the scan device, the volume of the object, or a state of a surface (e.g., an uneven surface).

According to embodiments of the present disclosure, a scan device may include a detachable ultrasonic probe, and thus can use a conventional ultrasonic probe in generating a 3D ultrasound image.

According to embodiments of the present disclosure, a body composition of an object, a three-dimensional distribution of the body composition, or a three-dimensional shape of fat and muscle can be analyzed based on a 3D ultrasound image of the object.

In addition, according to embodiments of the present disclosure, an internal shape of an object, such as a muscle layer, a fat layer, etc., in a 3D ultrasound image can be precisely recognized based on a deep learning model for semantic segmentation of target regions.

BRIEF DESCRIPTION OF THE DRAWINGS

The above and other aspects, features and advantages of the present disclosure will be more apparent from the following detailed description taken in conjunction with the accompanying drawings, in which:

FIG. 1 is a diagram briefly illustrating a configuration of an ultrasound imaging system according to an embodiment of the present disclosure;

FIG. 2 is a diagram illustrating an example of an ultrasound imaging system according to an embodiment of the present disclosure;

FIG. 3 is a diagram illustrating an example in which an object is inserted into a scan device in an ultrasound imaging system according to an embodiment of the present disclosure;

FIG. 4 is a diagram illustrating an example of control of the scan device illustrated in FIG. 2;

FIG. 5 is a diagram illustrating an INLET/OUTLET INTERFACE of a scan device in an ultrasound imaging system according to an embodiment of the present disclosure;

FIG. 6 is a diagram illustrating another example of a configuration of a scan device in an ultrasound imaging system according to an embodiment of the present disclosure, and FIG. 7 is a diagram illustrating an example of control of the scan device illustrated in FIG. 6;

FIG. 8 and FIG. 9 are diagrams illustrating an example of connection between an ultrasonic probe and a scan device in an ultrasound imaging system according to an embodiment of the present disclosure;

FIG. 10A and FIG. 10B are diagrams illustrating an example of an ultrasound image processing device in an ultrasound imaging system according to an embodiment of the present disclosure;

FIG. 11 to FIG. 16 are diagrams illustrating an example of image analysis in an ultrasound imaging system according to an embodiment of the present disclosure; and FIG. 17 is a flowchart illustrating an operation method of an ultrasound imaging system according to an embodiment of the present disclosure.

DETAILED DESCRIPTION OF THE EXEMPLARY EMBODIMENTS

The advantages and features of the present disclosure and ways to achieve them will be apparent by making reference to embodiments as described in detail in conjunction with the accompanying drawings. However, the present disclosure is not limited to the embodiments described below but may be implemented in various different ways, and it should be understood that the present disclosure includes all modifications, equivalents, or alternatives included in the spirit and scope of the present disclosure. The embodiments proposed below are provided in order to make the present disclosure complete and fully inform a person skilled in the art to which the present disclosure belongs, of the scope of the present disclosure. In describing the present disclosure, a detailed description of known relevant technologies incorporated herein will be omitted when it may make the subject matter of the present disclosure unclear.

The terms used in the present application are merely for the purpose of describing particular embodiments and are not intended to limit the present disclosure. A singular expression includes a plural expression unless they are definitely different in context. It will be understood that the terms "include" and/or "have," when used in the present application, specify the presence of stated features, numbers, stages, operations, elements, components, or a combination thereof, but do not preclude the possibility of presence or addition of one or more other features, numbers, stages, operations, elements, components, or combinations thereof. The terms such as "first" and "second" may be used to describe various elements, but the elements shall not be limited by the terms. These terms are used only to distinguish one element from another.

Hereinafter, embodiments according to the present disclosure will be described in detail with reference to the accompanying drawings. In describing the embodiments with reference to the accompanying drawings, the same or corresponding elements are denoted by the same reference numerals, and a repeated explanation thereof will be omitted.

FIG. 1 is a diagram briefly illustrating a configuration of an ultrasound imaging system according to an embodiment of the present disclosure.

Referring to FIG. 1, an ultrasound imaging system 100 according to an embodiment of the present disclosure may include a scan device 110 and an ultrasound image processing device 120. The ultrasound image processing device 120 may be used through installation of a program relating to an operation method of the ultrasound imaging system of the present disclosure in a conventional ultrasound image processing device, or may be a dedicated ultrasound image processing device designed to implement an operation method of the ultrasound imaging system of the present disclosure.

The scan device 110 may be configured to receive an object (e.g., an arm, a leg, or an abdomen part of a human body) inserted thereinto. The scan device 110 may include a hollow cylindrical body 111, a scan module 112, and an inlet/outlet interface 113.

The cylindrical body 111 may have an opening through which an object is insertable. The opening through which an object is inserted may be disposed on each of opposite sides of the cylindrical body 111. In addition, the cylindrical body 111 may be made of, for example, a flexible material (e.g., a high-elastic material such as latex) and an ultrasonic wave-transmitting material. The cylindrical body 111 is made of a flexible material, and thus the shape thereof may be freely transformed according to a change of the amount of an internal fluid introduced through the inlet/outlet interface 113.

In addition, the cylindrical body 111 is made of an ultrasonic wave-transmitting material, and thus enables transmission or reception of an ultrasonic signal between an object positioned in the cylindrical body and an ultrasonic probe 121 positioned outside of the same.

The scan module 112 connected to a part of the cylindrical body 111 may be configured to move the ultrasonic probe 121, which transmits or receives an ultrasonic signal to or from an object, to multiple positions at the scan device. Specifically, the scan module 112 may include a first frame, a second frame, a first motor, and a second motor. The first frame may be disposed along a circular circumference of the cylindrical body 111. The second frame may have a linear shape connected to one point of the first frame (wherein the connection includes both direct and indirect connections). The first and second frame is made of, for example, a steel material or plastic to maintain the shape thereof (e.g., a circular shape or an oval shape). In addition, the first motor may be configured to move the ultrasonic probe 121 along the first frame. The second motor may be configured to move the ultrasonic probe 121 along the second frame.

The inlet/outlet interface 113 connects the cylindrical body 111 and a fluid source (not illustrated) to enable a fluid to be injected into or discharged from the cylindrical body 111. For example, the inlet/outlet interface may include valves.

In addition, the scan device 110 may further include a pressure sensor (not illustrated) configured to measure the pressure of a fluid in the cylindrical body 111. A controller 140 of the ultrasound image processing device 120, which is configured to control the scan device 110, may be configured to control injection or discharge of a fluid into or from the cylindrical body 111 based on the pressure of the fluid, which is measured by the pressure sensor. For example, the controller 140 of the ultrasound image processing device 120 may be configured to: restrict injection of a fluid into the cylindrical body 111 based on a measured fluid pressure reaching a pre-configured reference pressure; cause discharge of the fluid from the cylindrical body 111 based on a measured fluid pressure exceeding the pre-configured reference pressure; or control injection or discharge of the fluid according to a pressure adjustment request (a user's request through a USER INPUT INTERFACE) from the ultrasound image processing device 120. That is, the controller 140 of the ultrasound image processing device 120 may be configured to cause the cylindrical body 111 in which an object is inserted to maintain a configured reference pressure, thereby allowing the cylindrical body 111 to come into close contact with the object without excessively pressing the object, regardless of the type of the object (e.g., an arm, a leg, or an abdomen part of a human body), the volume of the object, or a state of a surface (e.g., an uneven surface). As a result, the scan device 110 may prevent the occurrence of a space (e.g., an air layer in a path of transmission or reception of an ultrasonic signal) between an object and the cylindrical body 111, so as to increase a transfer rate of an ultrasonic signal to the object (or, an ultrasonic signal transmissivity of the cylindrical body).

The ultrasound image processing device 120 controlling the scan device 110 may include, for example, the ultrasonic probe 121, an ultrasonic transceiver 130, the controller 140, an image processor 150, a DISPLAY 160, a storage 170, a COMMUNICATION CIRCUIT 180, and a USER INPUT INTERFACE 190.

The ultrasonic probe 121 may be, for example, an 1D array type probe, but the present disclosure is not limited thereto. In addition, the ultrasonic probe 121 may be a linear type probe. However, the present disclosure is not limited thereto, and the ultrasonic probe may be of a convex type.

The ultrasonic probe 121 may be connected to the ultrasonic transceiver 130 (or the controller) by wire. However, the present disclosure is not limited thereto, and the ultrasonic probe may be wirelessly connected to the ultrasonic transceiver. The ultrasonic probe 121 may be connected to a part of the scan device 110 by being mounted to the scan device 110 or detachably held on a holding part in the scan device 110.

The ultrasonic probe 121 connected to a part of the scan device 110 may be configured to move to multiple positions at the scan device according to control of the ultrasound image processing device 120, emit a transmission ultrasonic signal to an object at the multiple positions, and receive a reflection ultrasonic signal reflected from the object. Specifically, the ultrasonic probe 121 may be configured to emit a transmission ultrasonic signal to an object according to a transmission signal applied from a transmitter 131 of the ultrasonic transceiver 130 according to control of the controller 140. In addition, the ultrasonic probe 121 may be configured to receive a reflection ultrasonic signal reflected from an object, and generate a reception signal. The ultrasonic probe 121 may be configured to generate a transmission ultrasonic signal through multiple transducers therein, or receive a reflection ultrasonic signal.

The ultrasonic transceiver 130 may include the transmitter 131 and a receiver 132. The transmitter 131 may be configured to generate a transmission signal according to control of the controller 140, or transfer the generated transmission signal to the ultrasonic probe 121. The receiver 132 may be configured to generate ultrasonic data by using a reception signal received from the ultrasonic probe 121, according to control of the controller 140, and transfer the generated ultrasonic data to the image processor 150. The controller 140 may be configured to control the receiver 132 to transfer a position associated with ultrasonic data (i.e., the position of the ultrasonic probe 121 relative to the scan device, which transmits or receives an ultrasonic signal in order to generate the ultrasonic data) together with the ultrasonic data to the image processor 150.

The controller 140 may be configured to control injection or discharge of a fluid into or from the cylindrical body 111 based on the pressure of the fluid in the cylindrical body, which is measured by the pressure sensor in the scan device 110, so as to prepare an optimal state in which an object can be scanned by using the ultrasonic probe 121. The controller 140 may include both a processor of the scan device 110 and a processor of the ultrasound image processing device 120.

The controller 140 may be configured to control the ultrasonic probe 121 to emit a transmission ultrasonic signal to an object at multiple positions at the scan device 110, and receive a reflection ultrasonic signal reflected from the object. The controller 140 may be configured to control the transmitter 131 to generate a transmission signal to be applied to each of multiple transducers based on a focus point and the positions of the multiple transducers included in the ultrasonic probe 121. In addition, the controller 140 may be configured to control the receiver 132 to perform analog-to-digital conversion of reception signals received from the ultrasonic probe 121, and add the digital-converted reception signals based on the focus point and the positions of the multiple transducers, so as to generate ultrasonic data. Controlling of the transmitter 131 or the receiver 132 may correspond to controlling of an operation timing of the transducers for transmission and reception of an ultrasonic signal.

In addition, the controller 140 may be configured to control the ultrasonic probe 121 to move to multiple positions at the scan device 110. The controller 140 may be configured to control the ultrasonic probe 121 to emit a transmission ultrasonic signal through the cylindrical body 111 to an object at multiple positions at the scan device 110, and control the ultrasonic probe 121 to receive a reflection ultrasonic signal that has been reflected from the object and has passed through the cylindrical body 111 at multiple positions at the scan device 110.

The controller 140 may be configured to control the first motor of the scan module 112 in the scan device 110 to move the ultrasonic probe 121 along the first frame of the scan module 112 from multiple positions on the second frame of the scan module 112. For example, the controller 140 may be configured to control the first motor to move the ultrasonic probe 121 from a first position on the second frame (e.g., an end point of the second frame) in a transverse direction by a set distance along the first frame. In addition, the controller 140 may be configured to control the first motor to move the ultrasonic probe 121 from a second position on the second frame (e.g., the point after moving from the end point of the second frame in a longitudinal direction by a set distance along the second frame) in a transverse direction by a set distance along the first frame.

In addition, the controller 140 may be configured to control the ultrasonic probe 121 to transmit a transmission ultrasonic signal at multiple positions on the second frame of the scan module 112 in the scan device 110 at which probing ranges of the ultrasonic probe overlap each other. Therefore, when the ultrasonic probe 121 moves in the longitudinal direction along the second frame, spacing between the probing ranges can be prevented, so as to enable an ultrasonic signal to be transferred to the entire area of an object.

In an embodiment, the controller 140 may be configured to control the first motor of the scan module 112 in the scan device 110 to move the ultrasonic probe 121 in different directions along the first frame of the scan module 112, from at least two different positions among multiple positions on the second frame of the scan module 112. A detailed description thereof will be described with reference to FIG. 4 below, for convenience of explanation.

In addition, the controller 140 may be configured to control overall operations of the ultrasound image processing device 120 and a signal flow between internal elements of the ultrasound image processing device 120. The controller 140 may include a memory configured to store data or a program for performing a function of the ultrasound image processing device 120, and a processor configured to process the data or the program. In addition, the controller 140 may be configured to receive a control signal from the USER INPUT INTERFACE 190 or an external device, and control an operation of the ultrasound image processing device 120 according to the control signal.

The image processor 150 may be configured to generate multiple two-dimensional (2D) ultrasound images of an object based on reflection ultrasonic signals received at multiple positions at the scan device 110, respectively. The image processor 150 may be configured to receive, from the receiver 132, ultrasonic data obtained through conversion of reflection ultrasonic signals received by the ultrasonic probe 121 at the positions, and generate multiple 2D ultrasound images of an object based on the received ultrasonic data. The image processor 150 may be configured to receive a position associated with ultrasonic data together with the ultrasonic data, and match the position to a 2D ultrasound image generated by using the ultrasonic data. The image processor 150 may be configured to store a 2D ultrasound image and a position matched to the 2D ultrasound image in the storage 170.

The image processor 150 may be configured to generate a 3D ultrasound image based on multiple 2D ultrasound images stored in the storage 170. The image processor 150 may be configured to connect multiple 2D ultrasound images based on positions matched to the 2D ultrasound images (i.e., the positions of the ultrasonic probe 121 relative to the scan device), to generate a 3D ultrasound image.

The image processor 150 may be configured to obtain state information of an object (e.g., a body composition per unit area, a three-dimensional distribution of a body composition, fat mass, muscle mass, or a three-dimensional shape of fat and muscle) based on a 3D ultrasound image, and output the state information through the DISPLAY 160, so as to enable precise identification of the inside of the three-dimensional object. The image processor 150 may be configured to apply, to a 3D ultrasound image, a deep neural network trained to find a body composition from multiple learning images, so as to rapidly and precisely detect (segment) a fat layer and a muscle layer of an object from the 3D ultrasound image, and obtain state information of the object based on the fat layer and the muscle layer of the object. In addition, the image processor 150 may be configured to analyze the texture of a fat layer and a muscle layer in a 3D ultrasound image so as to further obtain a qualitative state of fat and muscle as well as a quantitative state of fat and muscle as state information of an object.

The ultrasound imaging system of the present disclosure, which is capable of precisely providing a body composition through three-dimensional ultrasound image analysis, can be effectively used by a user (e.g., a bodybuilder or a sports player) who requires continuous monitoring of analysis of a precise body composition.

In an embodiment, the image processor 150 may be configured to obtain a body composition of an object based on a result of applying a 2D ultrasound image or a 2D section image generated from a 3D ultrasound image to a deep learning-based trained model which performs semantic segmentation. The trained model may include an encoder including a convolution filter, and a decoder including a transposed convolution filter.

The encoder may be configured to include a max pooling operation. In addition, the encoder may further include multiple channel attention modules including different size grids. There may be multiple grids, and the sizes of the multiple grids may decrease by a multiple of n (e.g., n is 2) in the direction in which the encoder performs encoding. The decoder may be configured to output a segmentation result. In addition, two feature maps included in an encoding process among multiple feature maps of the encoder may be connected to the decoder.

An example of applying a 2D section image to a deep learning-based trained model to analyze the image as described above will be described with reference to FIG. 11 to FIG. 16 below, for convenience of explanation.

The DISPLAY 160 may be configured to display a generated 3D ultrasound image and various pieces of information (e.g., state information of an object) which is processed by the ultrasound image processing device 120. The DISPLAY 160 may be implemented as a touch screen by being combined with, for example, a touch panel.

The storage 170 may be configured to store various data or programs for operating and controlling the ultrasound image processing device 120, input/output ultrasonic data, an acquired ultrasound image, etc.

The COMMUNICATION CIRCUIT 180 may include, for example, at least one of a wired communication module or a wireless communication module, and may be configured to enable communication with an external device (e.g., a server, a medical device, or a portable device (e.g., a smart phone, a tablet PC, a wearable device, etc.)).

The COMMUNICATION CIRCUIT 180 may be configured to receive a control signal from an external device, and transfer the received control signal to the controller 140 so as to allow the controller 140 to control the ultrasound image processing device 120 according to the received control signal. On the contrary, the COMMUNICATION CIRCUIT 180 may be configured to transmit a control signal received from the controller 140 to the external device so as to allow the external device to be operated according to the control signal, such that the controller 140 can control the external device.

A program for controlling the ultrasound image processing device 120 may be installed in the external device. The program may include an instruction to perform at least some of the operations of the controller 140. The program may be installed on the external device in advance, or a user of the external device can download and install the program from a server that provides the application.

The USER INPUT INTERFACE 190 may be configured to receive a user input to control the ultrasound image processing device 120. For example, a user input may include an input to control a button, a key pad, a mouse, a trackball, a jog switch, a knob, etc., an input to touch a touch pad or a touch screen, a voice input, a motion input, a biometric information input (e.g., iris recognition, fingerprint recognition, etc.), etc. However, the present disclosure is not limited thereto.

FIG. 2 is a diagram illustrating an example of an ultrasound imaging system according to an embodiment of the present disclosure. FIG. 3 is a diagram illustrating an example in which an object is inserted into a scan device in an ultrasound imaging system according to an embodiment of the present disclosure. FIG. 4 is a diagram illustrating an example of control of the scan device illustrated in FIG. 2. FIG. 5 is a diagram illustrating an INLET/OUTLET INTERFACE of a scan device in an ultrasound imaging system according to an embodiment of the present disclosure.

Referring to FIG. 2, an ultrasound imaging system according to an embodiment of the present disclosure may include a scan device 200 and an ultrasound image processing device 201.

The scan device 200 may include a hollow cylindrical body 210, a scan module 220, and an INLET/OUTLET INTERFACE 230. As illustrated in FIG. 3, the scan device 200 may be configured to receive an object, for example, an arm, a leg, or an abdomen part of a human body, inserted thereinto.

The cylindrical body 210 may have, for example, a tube shape with a certain height, and may include circular (or oval) openings 211 (opening_#1 211-1 and opening_#2 211-2), which are arranged on both sides of the cylindrical body, and into which an object can be inserted.

The scan module 220 may include first frames 221 (first frame_#1 221-1 and first frame_#2 221-2) disposed along both circular circumferences of the cylindrical body 210, and a second frame 222 which is linear and is connected to the first frames. The first frames 221 and the second frame 222 may be connected to each other so as to be perpendicular to each other.

In an embodiment, the first frames 221 may be arranged at both sides of the cylindrical body 210, respectively. However, the present disclosure is not limited thereto, and in another embodiment, a first frame may be disposed only at one side of the cylindrical body 210.

In addition, the scan module 220 may further include a first motor 223 configured to move an ultrasonic probe 240 in a transverse direction 225 (xy axis) along the first frames 221, and a second motor 224 configured to move the ultrasonic probe 240 in a longitudinal direction 226 (z axis) along the second frame 222. The first motor 223 may be configured to change the points at which the first frames 221 and the second frame 222 are connected, according to control of the ultrasound image processing device 201, to move the second frame 222, thereby moving the ultrasonic probe 240 connected (or mounted) to the second frame 222 in the transverse direction 225. That is, the first motor 223 may move the second frame 222 according to control of the ultrasound image processing device 201 so as to indirectly move the ultrasonic probe 240. In addition, the second motor 224 may be configured to change the point at which the ultrasonic probe 240 is connected (or mounted) to the second frame 222, according to control of the ultrasound image processing device 201, thereby moving the ultrasonic probe 240 in the longitudinal direction 226. That is, the second motor 224 may directly move the ultrasonic probe 240 according to control of the ultrasound image processing device 201.

The scan module 220 may repeatedly move the ultrasonic probe 240 in the transverse direction 225 by a set distance according to control of the ultrasound image processing device 201 to rotate the ultrasonic probe by 360 degrees with respect to an object, and then move the ultrasonic probe 240 in the longitudinal direction 226 by a set distance. Thereafter, the scan module 220 may repeatedly perform a 360-degree rotation through movement in the transverse direction 225 and a movement in the longitudinal direction 226 according to control of the ultrasound image processing device 201 so as to enable transmission or reception of an ultrasonic signal with respect to the entire area of the object.

For example, as illustrated in FIG. 4, the scan module 220 may move the ultrasonic probe 240 from a first position on the second frame 222 (e.g., an end point of the second frame) in a first transverse direction 225-1 by a set distance according to control of the ultrasound image processing device 201. The scan module 220 may repeatedly perform a movement in the first transverse direction 225-1 according to control of the ultrasound image processing device 201, to rotate the ultrasonic probe by 360 degrees with respect to an object, and then move the ultrasonic probe 240 in the longitudinal direction 226 by a set distance. Thereafter, the scan module 220 may move the ultrasonic probe 240-2 in a second transverse direction 225-2 by a set distance from a second position after the movement in the longitudinal direction 226, according to control of the ultrasound image processing device 201, so as to rotate the ultrasonic probe by 360 degrees with respect to the object.

When the ultrasonic probe 240 is moved, the ultrasound image processing device 201 may control the first motor 223 to move the ultrasonic probe 240 in different directions (i.e., the first transverse direction 225-1 and the second transverse direction 225-2) along the first frames 221, from the first position and the second position on the second frame 222, so as to prevent a communication wire of the ultrasonic probe 240 connected to the ultrasound image processing device 201 from being twisted due to the 360-degree rotation of the ultrasonic probe 240.

In an embodiment, according to control of the ultrasound image processing device 201, the scan module 220 may perform a 360-degree scan through repeated transverse movement of the ultrasonic probe 240 and then move the ultrasonic probe in a longitudinal direction. However, the present disclosure is not limited thereto, and the scan module may perform a linear scan through repeated longitudinal movement and then perform a transverse movement. When a linear scan is performed, the ultrasonic probe 240 may be moved at an inclination of, for example, 90 degrees.

In addition, in another embodiment, the scan module 220 may be configured to move the ultrasonic probe 240 according to a selected control method based on a result of comparison between a movement distance (rotation distance) in a transverse direction and a movement distance (linear distance) in a longitudinal direction, according to control of the ultrasound image processing device 201. For example, the ultrasound image processing device 201 may be configured to control the scan module 220 to move the ultrasonic probe 240 in a direction having a longer movement distance.

In addition, the ultrasound image processing device 201 may be configured to perform control such that a transmission ultrasonic signal is transmitted at multiple positions at which probing ranges of the ultrasonic probe overlap each other with respect to the second frame 222. Accordingly, as illustrated in FIG. 4, a probing range of the ultrasonic probe 240-1 existing at a first position (e.g., an end point of the second frame) on the second frame 222, and a probing range of the ultrasonic probe 240-2 existing at a second position (a point spaced a set distance apart from the first position) on the second frame 222 may overlap each other.

The INLET/OUTLET INTERFACE 230 connects the cylindrical body 210 and a fluid source to enable a fluid to be injected into or discharged from the cylindrical body 210. The INLET/OUTLET INTERFACE 230 is configured to, for example, as illustrated in FIG. 5, allow a discharge of fluid from the cylindrical body 210 so that the cylindrical body 210 is contracted and the thickness of the cylindrical body 210 is reduced (part (a) of FIG. 5), and allow an injection of fluid into the cylindrical body 210 so that the cylindrical body 210 is expanded and the thickness of the cylindrical body 210 is increased (part (b) of FIG. 5).

The ultrasound image processing device 201 may be configured to control the ultrasonic probe 240 to emit a transmission ultrasonic signal to an object at multiple positions at the scan device 200, and receive a reflection ultrasonic signal that is reflected from the object.

FIG. 6 is a diagram illustrating another example of a configuration of a scan device in an ultrasound imaging system according to an embodiment of the present disclosure. FIG. 7 is a diagram illustrating an example of control of the scan device illustrated in FIG. 6.

Referring to FIG. 6, a basic configuration of a scan device 600 is the same as that of a scan device described with reference to FIG. 2, and thus a description thereof will be omitted.

A scan module in the scan device 600 may include first frames 621 (first frame_#1 621-1 and first frame_#2 621-2) disposed along both circular circumferences of a cylindrical body, and a third frame 627 which is disposed in parallel to the first frames 621.

The scan module in the scan device 600 may further include a second frame 622 which is linear and is connected to the first frames 621 and the third frame 627.

In addition, the scan module in the scan device 600 may further include a first motor 623 configured to move an ultrasonic probe 640 in a transverse direction 625 along the first frames 621, and a second motor 624 configured to move the ultrasonic probe 640 in a longitudinal direction 626 along the second frame 622. The first motor 623 may be configured to change the point at which the ultrasonic probe 640 is connected (or mounted) to the third frame 627, according to control of an ultrasound image processing device 601, thereby moving the ultrasonic probe 640 in a transverse direction. That is, the first motor 623 may directly move the ultrasonic probe 640 according to control of the ultrasound image processing device 601. In addition, the second motor 624 may be configured to change the point at which the second frame 622 and the third frame 627 are connected, according to control of the ultrasound image processing device 201, to move the third frame 627, thereby moving the ultrasonic probe 640 connected (or mounted) to the third frame 627 in the longitudinal direction 626. That is, the second motor 624 may indirectly move the ultrasonic probe 640 according to control of the ultrasound image processing device 601.

For example, similar to the scan module illustrated in FIG. 2, the scan module in the scan device 600 may move the point at which the ultrasonic probe 640 is connected to the third frame 627, from a first position on the second frame 622 (e.g., an end point of the second frame) according to control of the ultrasound image processing device 601 as illustrated in FIG. 7, so as to move the ultrasonic probe 640 by a set distance in a transverse direction 625. In addition, the scan module in the scan device 600 may repeat a movement in the transverse direction 625 according to control of the ultrasound image processing device 601 to rotate the ultrasonic probe by 360 degrees with respect to an object, and then repeat an operation of moving the third frame 627 to move the ultrasonic probe 640 connected (or mounted) to the third frame 627 by a set distance in the longitudinal direction 626, so as to enable transmission or reception of an ultrasonic signal to or from the entire area of the object.

FIG. 8 and FIG. 9 are diagrams illustrating an example of connection between an ultrasonic probe and a scan device in an ultrasound imaging system according to an embodiment of the present disclosure.

Referring to FIG. 8, a scan device may include a coupling part, and may be connected to an ultrasonic probe by being coupled to the ultrasonic probe through the coupling part. Specifically, the scan device may, for example, couple a second coupling part 820 disposed on the ultrasonic probe (e.g., a side surface of the ultrasonic probe) to a first coupling part 810 disposed to be connected to a first motor (or a second motor) of a scan module, so as to detachably connect the ultrasonic probe. However, the present disclosure is not limited thereto, and a dedicated ultrasonic probe may be manufactured to be mounted to the scan module.

In addition, in another embodiment, as illustrated in FIG. 9, the scan device may include a holding part 910 disposed to be connected to the first motor (or the second motor) of the scan module, and a detachable ultrasonic probe may be held by the holding part 910. In this way, a conventional ultrasonic probe can be easily held on the scan module.

FIG. 10A and FIG. 10B are diagrams illustrating an example of an ultrasound image processing device in an ultrasound imaging system according to an embodiment of the present disclosure.

Referring to FIG. 10A, each of ultrasound image processing devices 1000a and 1000b may include a main DISPLAY 1010 and a sub DISPLAY 1020. One of the main DISPLAY 1010 or the sub DISPLAY 1020 may be implemented as a touch screen. The main DISPLAY 1010 and the sub DISPLAY 1020 may be configured to display an ultrasound image or various pieces of information processed by the ultrasound image processing devices 1000a and 1000b. In addition, the main DISPLAY 1010 and the sub DISPLAY 1020 may be implemented as a touch screen and provide a GUI, so as to receive data for controlling the ultrasound image processing devices 1000a and 1000b from a user. For example, the main DISPLAY 1010 may be configured to display an ultrasound image, and the sub DISPLAY 1020 may be configured to display a control panel in the form of a GUI, which is configured to control a display of the ultrasound image. The sub DISPLAY 1020 may receive data for controlling an image display, through the control panel displayed in the form of a GUI. Each of the ultrasound image processing devices 1000a and 1000b may be configured to control a display of an ultrasound image displayed on the main DISPLAY 1010 by using inputted control data.

Referring to FIG. 10B, the ultrasound image processing device 1000b may further include a control panel 1030 in addition to a main DISPLAY 1010 and a sub DISPLAY 1020. The control panel 1030 may include a button, a trackball, a jog switch, a knob, etc., and may be configured to receive data for controlling the ultrasound image processing device 1000b from a user. For example, the control panel 1030 may include a time gain compensation (TGC) button 1040, a freeze button 1050, etc. The TGC button 1050 may be configured to set a TGC value for each depth of an ultrasound image. In addition, the ultrasound image processing device 1000b may be configured to, when an input on the Freeze button 1050 is sensed in the process of scanning an ultrasound image, maintain a frame image displayed at the sensing time point.

The button, the trackball, the jog switch, and the knob, etc. included in the control panel 1030 may be provided as a GUI to the main DISPLAY 1010 or the sub DISPLAY 1020.

In another embodiment, an ultrasound image processing device may also be implemented as a portable type. Examples of a portable ultrasound image processing device may include a smart phone, a lap-top computer, a PDA, a tablet PC, and the like, which include a probe and an application. However, the present disclosure is not limited thereto.

Hereinafter, referring to FIG. 11 to FIG. 16, an example of image analysis in an ultrasound imaging system according to an embodiment of the present disclosure will be described.

An ultrasound image processing device in an ultrasound imaging system may generate multiple 2D ultrasound images by using multiple ultrasonic signals that are reflected from an object, and may generate a 3D ultrasound image based on the multiple 2D ultrasound images.

The ultrasound image processing device may obtain a body composition of an object based on a result of applying a 2D ultrasound image or a 2D section image generated from a 3D ultrasound image to a deep learning-based trained model which performs semantic segmentation. The ultrasound image processing device may detect, for example, a skin layer, a fat layer, and a muscle layer as illustrated in FIG. 11, based on a result of applying a 2D ultrasound image or a 2D section image to a deep learning-based trained model which performs semantic segmentation.

The trained model may include, as illustrated in FIG. 12, an encoder 1210 including a convolution filter, and a decoder 1220 including a transposed convolution filter. The encoder 1210 may further include an ReLU activation function, a group normalization (GN) filter, and a channel attention module together with the convolution filter.

The encoder 1210 may include multiple channel attention modules and grids having different sizes (the grids may be included in the channel attention modules). There may be multiple grids, and the sizes of the multiple grids may decrease by, for example, a multiple of 2 in the direction in which the encoder 1210 performs encoding.

In addition, the encoder 1210 may be configured to include a max pooling operation, and the decoder 1220 may be configured to output a segmentation result. Two feature maps included in an encoding process among multiple feature maps of the encoder 1210 may be connected to the decoder 1220.

In an embodiment, a channel attention module may be a channel attention module (CA with MSGRAP) based on multi-scale grid average pooling (MSGRAP). The channel attention module based on MSGRAP has a grid having a size changed (e.g., 10×10-8×8-6×6) from that of a grid used in a channel attention module based on grid average pooling (GRAP), and may be configured to use multiple grids having different sizes.

For reference, the channel attention module based on GRAP may perform, for example, a process as illustrated in FIG. 13. First, the channel attention module based on GRAP may obtain channel statistical information. The channel statistical information may be obtained by using k×k GRAP. In the GRAP, an input feature map may be divided into k×k grid cells having a pixel size of H/k and W/k. Pixels of each of the divided grid cells are averaged.

Statistical information for each channel ($z_c$) of an input feature map ($x_c$) may be obtained by [Equation 1].

$$z_c(i, j) = GRAP(x_c) = \frac{(k \times k)}{(H \times H)} \sum_{a=(H/k) \times i}^{(H/k) \times (i+1)} \sum_{b=(W/k) \times j}^{(W/k) \times (j+1)} x_c(a, b) \quad \text{[Equation 1]}$$

$x_c$ indicates a c-th channel of an input feature volume (x), and k is an average pooling grid size. In addition, a is the x coordinate of an input feature map, and b is the y coordinate of the input feature map. i is the x coordinate of a result image after GRAP, and j is the y coordinate of the result image. H is the height of the feature map, and W is the width of the feature map. H/k×W/k is a pixel size of each grid cell.

The obtained statistical information may be used to calculate dependency between a 1×1 convolution layer and two nonlinear activation functions (ReLU and sigmoid).

Thereafter, the channel attention module based on GRAP may obtain a scaling factor(s) by [Equation 2].

$$s + \Sigma(W_2 \delta(W_1 z)) \quad \text{[Equation 2]}$$

$\Sigma$ is a sigmoid nonlinear activation function, and $\delta$ is a rectified linear unit (ReLU) nonlinear activation function. $W_1 \in R^{C \times C/r}$ and $W_2 \in R^{C/r \times C}$ are weighted values of a 1×1 convolution layer. $z_c$ may be obtained through GRAP.

Thereafter, the channel attention module based on GRAP may obtain a c-th channel ($\hat{x}_c$) of a rescaled feature map by [Equation 3] by using the input feature map ($x_c$) and a c-th channel ($s_c$) of the scaling factor (s).

$$\hat{x}_c = U(s_c) \times x_c \quad \text{[Equation 3]}$$

× indicates pixel-wise multiplication, and U is an upsampling function.

The channel attention module based on GRAP may improve segmentation performance by using local information of an input image. To this end, the channel attention module based on GRAP may use, for example, a grid having a 10×10 size.

An encoder including a channel attention module based on GRAP may, for example, apply an ReLU activation function, a GN filter, a channel attention module based on GRAP, and a max pooling operation to an input image, as illustrated in part (a) of FIG. 14.

In addition, an encoder including a channel attention module based on MSGRAP may, for example, apply an ReLU activation function, a GN filter, a channel attention module based on MSGRAP, and a max pooling operation to an input image, as illustrated in part (b) of FIG. 14, and may apply a grid having a size changed from that of a grid used in a channel attention module based on GRAP, as the channel attention module based on MSGRAP.

The ultrasound imaging system, which is configured to apply a 2D section image to the trained model including the encoder 1210 using a channel attention module based on MSGRAP to obtain state information of an object, can improve semantic segmentation performance compared to use of other channel attention modules (e.g., FCN, U-NET, . . . , GAP, etc.) as illustrated in FIG. 15, and thus can precisely identify state information of an object. For example, an ultrasound imaging system using a channel attention module based on MSGRAP can obtain excellent results compared to use of other channel attention modules with respect to global accuracy, F1 score, sensitivity, specificity, precision, etc.

Such an ultrasound imaging system may apply, for example, a breast cancer ultrasound image to the trained model including the encoder 1210 using a channel attention module based on MSGRAP, and can perform a more precise segmentation of an ROI compared to use of other channel attention modules (e.g., FCN, U-NET, . . . , GAP, etc.), as illustrated in FIG. 16.

FIG. 17 is a flowchart illustrating an operation method of an ultrasound imaging system according to an embodiment of the present disclosure. The operation method of the ultrasound imaging system may be implemented by an ultrasound imaging system including a scan device and an ultrasound image processing device.

Referring to FIG. 17, in operation S1710, an object (e.g., an arm, a leg, or an abdomen part of a human body) may be inserted into a scan device in the ultrasound imaging system. The scan device may include a hollow cylindrical body having an opening through which an object is insertable, a scan module configured to move an ultrasonic probe, and an INLET/OUTLET INTERFACE through which a fluid can be injected into or discharged from the cylindrical body.

The cylindrical body may have an opening through which an object is insertable. The opening through which an object is inserted may be disposed on each of opposite sides of the cylindrical body. In addition, the cylindrical body may be made of, for example, a flexible material (e.g., a high-elastic material such as latex) and an ultrasonic wave-transmitting material. The cylindrical body is made of a flexible material, and thus the shape thereof may be freely transformed according to a change of the amount of an internal fluid introduced through the INLET/OUTLET INTERFACE. In addition, the cylindrical body is made of an ultrasonic wave-transmitting material, and thus enables transmission or reception of an ultrasonic signal between an object positioned in the cylindrical body and the ultrasonic probe positioned outside of the same.

The scan module connected to a part of the cylindrical body may be configured to move the ultrasonic probe, which transmits or receives an ultrasonic signal to or from an object, and place the ultrasonic probe at multiple positions at the scan device.

The scan module may include a first frame, a second frame, a first motor, and a second motor. The first frame may be disposed along a circular circumference of the cylindrical body. The second frame may have a linear shape connected to one point of the first frame. The first motor may be configured to move the ultrasonic probe along the first frame. The second motor may be configured to move the ultrasonic probe along the second frame.

In addition, the scan module may further include a coupling part or a holding part, and may be connected to an ultrasonic probe by being coupled to the ultrasonic probe through the coupling part or by enabling a detachable ultrasonic probe to be held by the holding part. In another embodiment, the scan module may be manufactured in a form in which a dedicated ultrasonic probe is mounted thereto.

The INLET/OUTLET INTERFACE connects the cylindrical body and a fluid source (not illustrated) to enable a fluid to be injected into or discharged from the cylindrical body.

In addition, the scan device may further include a pressure sensor configured to measure the pressure of a fluid in the cylindrical body.

In operation S1720, the ultrasound imaging system may adjust a degree of closeness between the scan device and the object by controlling the pressure of the scan device. The ultrasound imaging system may measure the pressure of a fluid in the cylindrical body through the pressure sensor of the scan device, and control injection or discharge of the fluid into or from the cylindrical body based on the measured pressure of the fluid.

In operation S1730, the ultrasound imaging system may control the ultrasonic probe connected to a part of the scan device to emit a transmission ultrasonic signal to the object at multiple positions at the scan device, and receive a reflection ultrasonic signal reflected from the object. Specifically, the ultrasound imaging system may control the ultrasonic probe to emit a transmission ultrasonic signal through the cylindrical body to the object at multiple positions at the scan device, and control the ultrasonic probe to receive a reflection ultrasonic signal that has been reflected from the object and has passed through the cylindrical body at multiple positions at the scan device.

The ultrasound imaging system may control the first motor to move the ultrasonic probe from multiple positions on the second frame along the first frame. For example, the ultrasound imaging system may control the first motor to move the ultrasonic probe from a first position on the second frame (e.g., an end point of the second frame) in a transverse direction by a set distance along the first frame. The ultrasound imaging system may repeatedly move the ultrasonic probe in a transverse direction by a set distance to rotate the ultrasonic probe by 360 degrees with respect to the object. In addition, the ultrasound imaging system may control the first motor to move the ultrasonic probe from a second position on the second frame (e.g., a point after moving from the end point of the second frame in a longitudinal direction by a set distance along the second frame) in a transverse direction by a set distance along the first frame.

The ultrasound imaging system may repeatedly perform, with respect to the ultrasonic probe, a 360-degree rotation through movement in the transverse direction and a movement in the longitudinal direction so as to enable transmission or reception of an ultrasonic signal with respect to the entire area of the object.

The ultrasound imaging system may control the first motor to move the ultrasonic probe in different directions along the first frame, from at least two different positions among multiple positions on the second frame. For example, the ultrasound imaging system may control the ultrasonic probe positioned at the first position on the second frame and the ultrasonic probe positioned at the second position thereon to be rotated by 360 degrees in different directions, so as to prevent a communication wire of the ultrasonic probe 240 from being twisted due to the repeated rotation.

In addition, in an embodiment, the ultrasound imaging system may control the ultrasonic probe to transmit a transmission ultrasonic signal at multiple positions on the second frame of the scan device at which probing ranges of the ultrasonic probe overlap each other. Therefore, when the ultrasonic probe moves in the longitudinal direction along the second frame, spacing between the probing ranges can be prevented, so as to enable an ultrasonic signal to be transferred to the entire area of an object.

In operation S1740, the ultrasound imaging system may generate multiple two-dimensional ultrasound images based on reflection ultrasonic signals received at multiple positions at the scan device, respectively. The ultrasound imaging system may generate a 2D ultrasound image in association with the reception of a reflection ultrasonic signal at each of the positions at the scan device, and may match the position of the ultrasonic probe having received a reflection ultrasonic signal with a 2D ultrasound image, and store the position and the image in a storage.

In operation S1750, the ultrasound imaging system may generate a 3D ultrasound image based on the multiple 2D ultrasound images. The ultrasound imaging system may generate a 3D ultrasound image based on multiple positions (positions at each of which an ultrasonic signal used to generate a 2D ultrasound image is transmitted or received) matched with multiple 2D ultrasound images, respectively, and the multiple 2D ultrasound images.

In operation S1760, the ultrasound imaging system may analyze the 3D ultrasound image. The ultrasound imaging system may obtain state information (e.g., a body composition, a three-dimensional distribution of a body composition, fat mass, muscle mass, or a three-dimensional shape of fat and muscle) of the object based on the 3D ultrasound image, and output the state information. The ultrasound imaging system may apply, to a 3D ultrasound image, a deep neural network trained to find a body composition from multiple learning images, so as to rapidly and precisely detect a fat layer and a muscle layer of an object from the 3D ultrasound image, and obtain state information of the object based on the fat layer and the muscle layer of the object.

The use of the terms "a", "an", and "the" and similar referents in the specification (especially in the following claims) of the present disclosure are to be construed to cover both the singular and the plural. Furthermore, recitation of ranges provided herein is intended to serve a disclosure to which individual values falling within the range are applied (unless otherwise indicated herein), and each individual value included in the range is incorporated into the detailed description as if it were recited herein.

Also, the operations of all methods described herein can be performed in any suitable order unless otherwise indicated herein or otherwise clearly contradicted by context. The present disclosure is not limited to the described order of the operations. The use of any and all examples or exemplary terms (e.g., "such as" or "etc.") provided herein, is intended merely to better illuminate the present disclosure and does not pose a limitation on the scope of the present disclosure unless otherwise claimed. Further, those skilled in the art will understand that various modifications, combinations, and changes may be made according to design conditions and factors within the scope of the appended claims or their equivalents.

Accordingly, the spirit of the present disclosure should not be limited and determined by the embodiments described above, and it should be noted that not only the claims described below but also their equivalents fall within the spirit and scope of the present disclosure.

What is claimed is:

1. An ultrasound imaging system comprising:
a scan device comprising a cylindrical body having an opening through which an object is insertable;
an ultrasonic probe connected to a part of the scan device;
a controller configured to control the ultrasonic probe to emit a transmission ultrasonic signal to the object at multiple positions at the scan device, and receive a reflection ultrasonic signal reflected from the object; and
an image processor configured to generate multiple two-dimensional (2D) ultrasound images based on reflection ultrasonic signals received at the multiple positions at the scan device, respectively, and generate a 3D ultrasound image based on the multiple 2D ultrasound images, wherein the scan device further comprises a scan module configured to move the ultrasonic probe,
wherein the scan module comprises:
a plurality of first frames disposed along a circular circumference of the cylindrical body;
a second frame which is linear and is connected to one point of each of the plurality of first frames;
a first motor configured to move the ultrasonic probe along each of the plurality of first frames; and
a second motor configured to move the ultrasonic probe along the second frame;
wherein the controller is configured to:
control the second motor to move the ultrasonic probe to a first position among a plurality of positions of the second frame;
control the first motor to move the ultrasonic probe at the first position in a first direction along a first frame corresponding to the first position among the plurality of first frames;
control the second motor to move the ultrasonic probe to a second position among the plurality of positions of the second frame, the second position being different from the first position; and
control the first motor to move the ultrasonic probe at the second position in a second direction along a first frame corresponding to the second position among the plurality of first frames, the second direction being different from the first direction.

2. The ultrasound imaging system of claim 1, wherein the scan device further comprises:
an INLET/OUTLET INTERFACE through which a fluid can be injected into or discharged from the cylindrical body,
wherein the cylindrical body is made of a flexible material.

3. The ultrasound imaging system of claim 2, wherein the controller is configured to:
control the ultrasonic probe to move to the multiple positions at the scan device;
control the ultrasonic probe to emit the transmission ultrasonic signal through the cylindrical body to the object at the multiple positions at the scan device; and
control the ultrasonic probe to receive the reflection ultrasonic signal that has been reflected from the object and has passed through the cylindrical body at the multiple positions at the scan device.

4. The ultrasound imaging system of claim 1, wherein the controller is configured to control the transmission ultrasonic signal to be transmitted at multiple positions on the second frame at which probing ranges of the ultrasonic probe overlap each other.

5. The ultrasound imaging system of claim 2, wherein the scan device further comprises a pressure sensor configured to measure a fluid pressure of the cylindrical body, and
the controller is configured to control injection or discharge of the fluid into or from the cylindrical body based on the measured fluid pressure.

6. The ultrasound imaging system of claim 1, wherein the ultrasonic probe is connected to the scan device by being mounted to the scan device or detachably held on a holding part in the scan device.

7. The ultrasound imaging system of claim 1, wherein the image processor is configured to obtain a body composition of the object based on the 3D ultrasound image.

8. The ultrasound imaging system of claim 7, wherein the image processor is configured to obtain the body composition of the object based on a result of applying a 2D ultrasound image or a 2D section image generated from the 3D ultrasound image to a deep learning-based trained model which performs semantic segmentation.

9. The ultrasound imaging system of claim 8, wherein the trained model comprises an encoder including a convolution filter, and a decoder including a transposed convolution filter,
wherein the encoder is configured to include a max pooling operation,
the decoder is configured to output a segmentation result, and
two feature maps included in an encoding process among multiple feature maps of the encoder are connected to the decoder.

10. The ultrasound imaging system of claim 8,
wherein the trained model comprises an encoder including a convolution filter, and a decoder including a transposed convolution filter, and
the encoder comprises multiple channel attention modules including different size grids.

11. The ultrasound imaging system of claim 10, wherein there are multiple grids, and sizes of the multiple grids decrease in a direction in which the encoder performs encoding.

12. An operation method of an ultrasound imaging system for generating a 3D ultrasound image of an object inserted in a scan device, the method comprising:
controlling an ultrasonic probe connected to a part of the scan device to emit a transmission ultrasonic signal to the object at multiple positions at the scan device, and receive a reflection ultrasonic signal reflected from the object; and
generating multiple 2D ultrasound images based on reflection ultrasonic signals received at the multiple positions at the scan device, respectively, and generating a 3D ultrasound image based on the multiple 2D ultrasound images,
wherein the scan device further comprises a scan module configured to move the ultrasonic probe,
wherein the scan module comprises:
a plurality of first frames disposed along a circular circumference of the cylindrical body; and
a second frame which is linear and is connected to one point of each of the plurality of first frames,
wherein the controlling the ultrasonic probe comprises:
moving the ultrasonic probe to a first position among a plurality of positions of the second frame;
moving the ultrasonic probe at the first position in a first direction along a first frame corresponding to the first position among the plurality of first frames;
moving the ultrasonic probe to a second position among the plurality of positions of the second frame, the second position being different from the first position; and
moving the ultrasonic probe at the second position in a second direction along a first frame corresponding to the second position among the plurality of first frames, the second direction being different from the first direction.

* * * * *